United States Patent
Hishikawa et al.

(10) Patent No.: US 10,180,413 B2
(45) Date of Patent: Jan. 15, 2019

(54) INK COMPOSITION FOR PLASMA PROCESSING DETECTION, AND INDICATOR FOR PLASMA PROCESSING DETECTION USING SAID INK COMPOSITION

(71) Applicant: SAKURA COLOR PRODUCTS CORPORATION, Osaka-shi, Osaka (JP)

(72) Inventors: Keita Hishikawa, Osaka (JP); Kazuhiro Uneyama, Osaka (JP)

(73) Assignee: SAKURA COLOR PRODUCTS CORPORATION, Osaka-shi (JP)

( * ) Notice: Subject to any disclaimer, the term of this patent is extended or adjusted under 35 U.S.C. 154(b) by 0 days.

(21) Appl. No.: 15/529,382

(22) PCT Filed: Nov. 24, 2015

(86) PCT No.: PCT/JP2015/082841
§ 371 (c)(1),
(2) Date: May 24, 2017

(87) PCT Pub. No.: WO2016/088595
PCT Pub. Date: Jun. 9, 2016

(65) Prior Publication Data
US 2017/0261476 A1    Sep. 14, 2017

(30) Foreign Application Priority Data
Dec. 2, 2014 (JP) .................................. 2014-244414

(51) Int. Cl.
*G01N 31/22* (2006.01)
*C09D 11/50* (2014.01)
(Continued)

(52) U.S. Cl.
CPC ............. *G01N 31/22* (2013.01); *C01G 31/02* (2013.01); *C09D 11/037* (2013.01); *C09D 11/10* (2013.01);
(Continued)

(58) Field of Classification Search
CPC .... G01N 21/78; G01N 31/226; G01N 31/223; G01N 21/718; G01N 21/75;
(Continued)

(56) References Cited

U.S. PATENT DOCUMENTS

| | | | |
|---|---|---|---|
| 4,155,895 A | 5/1979 | Rohowetz et al. | |
| 4,179,397 A | 12/1979 | Rohowetz et al. | |

(Continued)

FOREIGN PATENT DOCUMENTS

| | | |
|---|---|---|
| CN | 1877777 A | 12/2006 |
| CN | 101014668 A | 8/2007 |

(Continued)

OTHER PUBLICATIONS

International Search Report dated Feb. 9, 2016, issued in counterpart of International Application No. PCT/JP2015/082841 (2 pages).
(Continued)

*Primary Examiner* — Jennifer Wecker
(74) *Attorney, Agent, or Firm* — Westerman, Hattori, Daniels & Adrian, LLP (57) ABSTRACT

The present invention provides an ink composition for forming a color-changing layer that changes color by plasma treatment, the ink composition exhibiting excellent heat resistance, with the gasification of the color-changing layer or the scattering of the fine debris of the color-changing layer caused by plasma treatment being suppressed to the extent that electronic device properties are not affected. The invention provides an ink composition for forming a color-changing layer that changes color by plasma treatment, the (Continued)

ink composition comprising metal oxide particles containing at least one element selected from the group consisting of Mo, W, Sn, V, Ce, Te, and Bi, and a binder resin.

16 Claims, 1 Drawing Sheet

(51) Int. Cl.

| | | |
|---|---|---|
| G01N 21/75 | (2006.01) | |
| G01N 21/78 | (2006.01) | |
| C01G 31/02 | (2006.01) | |
| H05H 1/00 | (2006.01) | |
| C09D 11/037 | (2014.01) | |
| C09D 11/10 | (2014.01) | |
| H01L 21/67 | (2006.01) | |
| H01J 37/244 | (2006.01) | |
| C23C 28/00 | (2006.01) | |
| H01L 21/3213 | (2006.01) | |
| C01G 39/02 | (2006.01) | |
| C01G 29/00 | (2006.01) | |
| C23C 24/08 | (2006.01) | |
| C01G 41/02 | (2006.01) | |

(52) U.S. Cl.
CPC ............. *C09D 11/50* (2013.01); *G01N 21/75* (2013.01); *G01N 21/78* (2013.01); *G01N 21/783* (2013.01); *G01N 31/223* (2013.01); *G01N 31/226* (2013.01); *H05H 1/00* (2013.01); *C01G 29/00* (2013.01); *C01G 39/02* (2013.01); *C01G 41/02* (2013.01); *C23C 24/085* (2013.01); *C23C 28/322* (2013.01); *C23C 28/345* (2013.01); *G01N 2021/751* (2013.01); *H01J 37/244* (2013.01); *H01L 21/32136* (2013.01)

(58) Field of Classification Search
CPC .......... H01L 21/32136; H01L 21/3065; C01G 29/00; C01G 31/02; C01G 39/02; C01G 41/02; C23C 16/50; C23C 16/52
See application file for complete search history.

(56) References Cited

U.S. PATENT DOCUMENTS

| | | | |
|---|---|---|---|
| 4,839,311 A | | 6/1989 | Riley et al. |
| 5,955,025 A | | 9/1999 | Barrett |
| 5,990,199 A | | 11/1999 | Bealing et al. |
| 6,063,631 A | | 5/2000 | Ignacio |
| 6,117,685 A | | 9/2000 | Omatsu et al. |
| 6,267,242 B1 | | 7/2001 | Nagata et al. |
| 6,355,448 B1 | | 3/2002 | Foltz et al. |
| 6,410,338 B1 | | 6/2002 | Lippold et al. |
| 6,524,763 B1 | | 2/2003 | Kuroda et al. |
| 6,852,281 B2 | | 2/2005 | Inoue et al. |
| 7,189,355 B2 | | 3/2007 | Mikumo et al. |
| 7,364,700 B2 | | 4/2008 | Maruo et al. |
| 7,364,770 B2 | | 4/2008 | Nagashima et al. |
| 7,976,781 B2 | | 7/2011 | Maruo et al. |
| 7,981,687 B2 | | 7/2011 | Yamaguchi et al. |
| 8,222,327 B2 | | 7/2012 | Mikumo et al. |
| 8,530,242 B2 | | 9/2013 | Lin et al. |
| 2001/0054374 A1 | | 12/2001 | Omatsu et al. |
| 2002/0051733 A1 | | 5/2002 | Antonoplos et al. |
| 2002/0121629 A1 | | 9/2002 | Mikumo et al. |
| 2005/0054374 A1 | | 3/2005 | Namiki |
| 2006/0194056 A1 | | 8/2006 | Nagashima et al. |
| 2006/0244379 A1 | | 11/2006 | Shin |
| 2006/0283746 A1 | | 12/2006 | Sutoh et al. |
| 2008/0090726 A1* | | 4/2008 | Eskra ............... B41M 5/385 503/207 |
| 2008/0267811 A1* | | 10/2008 | Yamaguchi ........ G01N 31/223 422/3 |
| 2009/0212237 A1 | | 8/2009 | Sugiki et al. |
| 2010/0119410 A1 | | 5/2010 | Yamaguchi et al. |
| 2011/0009535 A1 | | 1/2011 | Mikumo et al. |
| 2011/0065203 A1 | | 3/2011 | Studer et al. |
| 2011/0275159 A1* | | 11/2011 | Landgrebe ............. A61L 2/28 436/1 |
| 2011/0312096 A1 | | 12/2011 | Whitman et al. |
| 2012/0100395 A1 | | 4/2012 | Feiler et al. |
| 2012/0315659 A1* | | 12/2012 | Andreescu ............ C12Q 1/26 435/25 |
| 2014/0154808 A1* | | 6/2014 | Patel ..................... G01K 3/04 436/1 |
| 2015/0050745 A1* | | 2/2015 | Karato ................ G01N 31/226 436/135 |
| 2016/0045631 A1 | | 2/2016 | Yamaguchi et al. |
| 2016/0133444 A1 | | 5/2016 | Oshiro et al. |
| 2016/0141192 A1* | | 5/2016 | Uneyama ............... G01N 21/78 116/201 |
| 2016/0349222 A1 | | 12/2016 | Mori |
| 2017/0044389 A1 | | 2/2017 | Mori |
| 2017/0101548 A1 | | 4/2017 | Mori et al. |
| 2017/0153174 A1 | | 6/2017 | Yamakawa et al. |
| 2017/0261476 A1 | | 9/2017 | Hishikawa et al. |
| 2017/0330777 A1 | | 11/2017 | Hishikawa et al. |

FOREIGN PATENT DOCUMENTS

| | | | |
|---|---|---|---|
| EP | 1312918 | A2 | 5/2003 |
| GB | 2 168 082 | | 6/1986 |
| JP | 63-36786 | A | 2/1988 |
| JP | S63-36876 | A | 2/1988 |
| JP | 1-295423 | A | 11/1989 |
| JP | 4-305492 | A | 10/1992 |
| JP | 6-69165 | A | 3/1994 |
| JP | 7-26477 | A | 1/1995 |
| JP | 11-37988 | A | 2/1999 |
| JP | 2000-269191 | A | 9/2000 |
| JP | 2001-174449 | A | 6/2001 |
| JP | 2001-237097 | A | 8/2001 |
| JP | 2001-242249 | A | 9/2001 |
| JP | 2002-011081 | A | 1/2002 |
| JP | 2002-022534 | A | 1/2002 |
| JP | 2002-502953 | A | 1/2002 |
| JP | 2002-303618 | A | 10/2002 |
| JP | 2002-322315 | A | 11/2002 |
| JP | 2002-323451 | A | 11/2002 |
| JP | 2003-506156 | A | 2/2003 |
| JP | 2003-515744 | A | 5/2003 |
| JP | 2003-325646 | A | 11/2003 |
| JP | 2004-101488 | A | 4/2004 |
| JP | 2004-146738 | A | 5/2004 |
| JP | 2004-146739 | A | 5/2004 |
| JP | 2004-203984 | A | 7/2004 |
| JP | 2004-298479 | A | 10/2004 |
| JP | 2005-111154 | A | 4/2005 |
| JP | 2005-142287 | A | 6/2005 |
| JP | 2005-315828 | A | 11/2005 |
| JP | 2005-329019 | A | 12/2005 |
| JP | 2006-78463 | A | 3/2006 |
| JP | 2006-223351 | A | 8/2006 |
| JP | 2007-40785 | A | 2/2007 |
| JP | 2008-125760 | A | 6/2008 |
| JP | 2009-213609 | A | 9/2009 |
| JP | 2010-501655 | A | 1/2010 |
| JP | 2011-530085 | A | 12/2011 |
| JP | 2012/050664 | A | 3/2012 |
| JP | 2012-068811 | A | 4/2012 |
| JP | 2012-78202 | A | 4/2012 |
| JP | 2013-95764 | A | 5/2013 |
| JP | 2013-95765 | A | 5/2013 |
| JP | 2013-98196 | A | 5/2013 |
| JP | 2013098196 | A | * 5/2013 |
| JP | 2013-233387 | A | 11/2013 |
| JP | 2014-109523 | A | 6/2014 |
| JP | 2016-111063 | A | 6/2016 |
| WO | 98/46279 | A1 | 10/1998 |

(56) References Cited

FOREIGN PATENT DOCUMENTS

| WO | 98/46994 | A1 | 10/1998 |
|---|---|---|---|
| WO | 99/39754 | A1 | 8/1999 |
| WO | 01/10476 | A1 | 2/2001 |
| WO | 01/40792 | A1 | 6/2001 |
| WO | 2004-087222 | A1 | 10/2004 |
| WO | 2006/109726 | A1 | 10/2006 |
| WO | 2008/022952 | A1 | 2/2008 |
| WO | 2013/129473 | A1 | 9/2013 |
| WO | 2014/038612 | A | 3/2014 |
| WO | 2014/196440 | A1 | 12/2014 |
| WO | 2015/025699 | A1 | 2/2015 |
| WO | 2015/170592 | A1 | 11/2015 |

OTHER PUBLICATIONS

ISR dated Jul. 14, 2015 issued in International Application No. PCT/JP2015/062244 (2 pp).
Non-Final Offce Action dated Mar. 1, 2018, issued in U.S. Appl. No. 15/305,822, (7 pp).
Notice of Allowance dated Mar. 22, 2018, issued in U.S. Appl. No. 15/316,980, (18 pp).
English Translation of JP2002/303618, Oct. 2002; (14 pp) cited in Non-Final Office Action dated Mar. 1, 2018 for U.S. Appl. No. 15/305,822.
English Translation of JP 2004/101488, Apr. 2004 (9 pp) cited in Non-Final Office Action dated Mar. 1, 2018 for U.S. Appl. No. 15/305,822.
English Translation of WO 2014/038612, Mar. 2014 (10 pp) cited in Non-Final Office Action dated Mar. 1, 2018 for U.S. Appl. No. 15/305,822.
Janus Green B, no date available; https://pubchem.ncbi.nlm.nih.gov/compound/Janus_green_B (17 pp) in Non-Final Office Action dated Mar. 1, 2018 for U.S. Appl. No. 15/305,822.
Bakelite BKUA 2370, Georgia Pacific Chemicals Phenolic Resins, no date available, http://www.brenntag.com/specialties/en/product-industries/industries/material-science/composites-and-advanced-materials/georgia-pacific-phenolic-resins-dispersions-composites.jsp (3 pp) cited in Non-Final Office Action dated Mar. 1, 2018 for U.S. Appl. No. 15/305,822.
Sylowhite SM 405, Jul. 2009, http://novana.ch/news/8/3/0/sylowhite-sm-405 (1 page) cited in Non-Final Office Action dated Mar. 1, 2018 for U.S. Appl. No. 15/305, 822.
Final Office Action dated Nov. 17, 2017, issued in U.S. Appl. No. 15/305,822, (13 pages).
International Search Report dated Apr. 14, 2015, issued in counterpart International Application No. PCT/JP2015/053742 (1 page).
Masaaki Nagatsu, Plasma Sterilization, Journal of Plasma and Fusion Research, 2007, vol. 83, No. 7, pp. 601-606.
Notice of Allowance dated Nov. 22, 2017, issued in U.S. Appl. No. 15/316,980 (15 pages).
Final Office Action dated Nov. 17, 2017, issued in U.S. Appl. No. 14/895,835 (18 pages).
International Search Report dated Sep. 2, 2014, issued in Application No. PCT/JP2014/064209 (4 pages).
English translation of Written Opinion dated Nov. 17, 2015, issued in counterpart Application No. PCT/JP2015/073769 (4 pages).
International Search Report dated Nov. 17, 2015, issued in Application No. PCT/JP2015/073769 (3 pages).
Non-Final OA dated Jun. 28, 2017, issued in U.S. Appl. No. 14/895,835 (19 pages).
Non-Final OA dated Jun. 30, 2017, issued in U.S. Appl. No. 15/316,980 (20 pages).
International Search Report dated Jul. 14, 2015, issued in counterpart International Application No. PCT/JP2015/061545 (4 pages).
Non-Final OA dated Jul. 3, 2017, issued in U.S. Appl. No. 15/305,822 (11 pages).
International Search Report dated Sep. 16, 2014, issued in counterpart Application No. PCT/JP2014/070419 (2 pages).

Office Action dated Mar. 14, 2017, issued in Chinese Application No. 201480033301.2, with partial English translation (11 pages).
Office Action dated Jun. 9, 2010, issued in counterpart Japanese Application No. 2005-064179 (2 pages).
International Search Report dated May 17, 2005, issued in Application No. PCT/JP2005/006138 (1 page).
Non-Final Office Action dated Mar. 4, 2009, issued in U.S. Appl. No. 10/594,587 (9 pages).
Final Office Action dated Nov. 27, 2009, issued in U.S. Appl. No. 10/594,587 (11 pages).
Non-Final OA dated Jun. 11, 2010, issued in U.S. Appl. No. 10/594,587 (6 pages).
Final Office Action dated Dec. 23, 2010, issued in U.S. Appl. No. 10/594,587 (5 pages).
Notice of Allowance dated Apr. 1, 2011, issued in U.S. Appl. No. 10/594,587 (7 pages).
Final Office Action dated Nov. 17, 2017, issued in U.S. Appl. No. 15/305,822 (9 pages).
Non-Final Office Action dated Dec. 19, 2017, issued in U.S. Appl. No. 15/309,510 (16 pages).
Non-Final Office Action dated Nov. 20, 2017, issued in U.S. Appl. No. 14/897,461 (27 pages).
Notice of Allowance dated May 1, 2018, issued in U.S. Appl. No. 14/897,461 (27 pages).
Notice of Allowance dated Apr. 27, 2018, issued in U.S. Appl. No. 15/309,510 (24 pages).
International Search Report dated Mar. 1, 2016, issued in counterpart International Application No. PCT/JP2015/082818 (2 pages).
Office Action dated Sep. 28, 2010, issued in counterpart Japanese Application No. 2005-064179, with English translation (5 pages).
Office Action dated Mar. 26, 2013, issued in counterpart Japanese Application No. 2010-263654, with English translation (5 pages).
Office Action dated Mar. 20, 2018, issued in counterpart Japanese Application No. 2014-087638, with English translation (9 pages).
Notice of Allowance dated May 17, 2018, issued in U.S. Appl. No. 15/117,601 (28 pages).
Notice of Allowance dated Sep. 6, 2018, issued in U.S. Appl. No. 15/309,510 (22 pages).
Kitaoka, Kyozo, "Guide for Coatings to Synthetic Resin", May 25, 1974, First Edition, pp. 212-213, with English translation; Cited in Japanese Office Action dated Aug. 21, 2018.
"Toryo Genryo Binran [Paint Material Handbook]", Japan Paint Manufacturers Association, May 31, 1999, 7th Edition, pp. 77-79, with English translation; Cited in Japanese Office Action dated Aug. 21, 2018.
Office Action dated Aug. 21, 2018, issued in Japanese Application No. 2014-087638, with English translation (7 pages).
Notice of Allowance dated Jun. 13, 2018, issued in U.S. Appl. No. 15/316,980 (19 pages).
Notice of Allowance dated Aug. 7, 2018, issued in U.S. Appl. No. 15/305,822 (18 pages).
Non-Final Office Action dated May 17, 2018, issued in U.S. Appl. No. 15/117,601 (28 pages).
Office Action dated Aug. 28, 2018, issued in counterpart Japanese Application No. 2015-532792, with English tranlsation (6 pages).
Office Action dated Sep. 5, 2018, issued in counterpart Chinese Application No. 201580020478.3, with English translation (12 pages).
Office Action dated Oct. 9, 2018, issued in counterpart Japanese Application No. 2015-562838, with English translation (5 pages).
Office Action dated Oct. 9, 2018, issued in counterpart Japanese Application No. 2014-244414, with English translation (7 pages).
Final Office Action dated Sep. 20, 2018, issued in U.S. Appl. No. 15/117,601 (21 pages).
Final Office Action dated Oct. 29, 2018, issued in U.S. Appl. No. 15/117,601 (15 pages).
Office Action dated Dec. 4, 2018, issued in counterpart Japanese Application No. 2015-095244, with English translation (5 pages).

* cited by examiner

FIG. 3

INK COMPOSITION FOR PLASMA PROCESSING DETECTION, AND INDICATOR FOR PLASMA PROCESSING DETECTION USING SAID INK COMPOSITION

TECHNICAL FIELD

The present invention relates to an ink composition for detecting plasma treatment and a plasma treatment detection indicator using the ink composition. In particular, the present invention relates to an ink composition for detecting plasma treatment using metal oxide particles as a color-changing component, and to a plasma treatment detection indicator using the ink composition, the indicator being useful as an indicator for use in an electronic device production equipment.

BACKGROUND ART

In the production process of electronic devices, a variety of treatments have been performed on the electronic device substrate (substrate to be treated). In the case of, for example, a semiconductor as the electronic device, a semiconductor wafer (wafer) is loaded; after that, a film-forming step of forming an insulating film or a metal film, a photolithography step of forming a photoresist pattern, an etching step of processing the film using the photoresist pattern, an impurity-adding step of forming a conductive layer on the semiconductor wafer (also called doping or diffusion process), a CMP step of polishing the uneven surface of the film to flatten the surface (chemical mechanical planarization), and the like are performed, followed by semiconductor wafer electrical characteristics inspection for inspecting the finish of the pattern or the electrical characteristics (these steps may be collectively referred to as the front-end process). Subsequently, the back-end process of forming semiconductor chips follows. This front-end process is also performed not only when the electronic device is a semi conductor, but also when other electronic devices (e.g., light-emitting diodes (LED), solar batteries, liquid crystal displays, and organic EL (Electro-Luminescence) display) are produced.

The front-end process includes, in addition to the steps described above, a washing step using plasma, ozone, ultraviolet rays, and the like, and a step of removing a photoresist pattern using plasma, radical-containing gas, and the like (also called ashing or ash removal). The film-forming step also includes CVD for forming a film by chemically reacting a reactive gas on the wafer surface, and sputtering for forming a metal film. The etching step includes, for example, dry etching performed by chemical reaction in plasma, and etching by ion beams. The "plasma" refers to the state in which gas is dissociated, and ions, radicals, and electrons are present in the plasma.

In the production process of electronic devices, the various treatments described above must be properly performed to secure the performance, reliability, and the like of electronic devices. Thus, in the plasma treatment represented by a film-forming step, an etching step, an ashing step, an impurity-adding step, a washing step, etc., a completion check and the like is performed to confirm the completion of the plasma treatment, for example, by emission analysis of plasma with a spectrometer, or by using a plasma treatment detection indicator comprising a color-changing layer that changes color in a plasma treatment atmosphere.

As an example of the plasma treatment detection indicator, Patent Literature 1 discloses an ink composition for detecting a plasma treatment comprising 1) at least one of anthraquinone colorants, azo colorants, or phthalocyanine colorants; and 2) at least one of binder resins, cationic surfactants, or extenders, wherein a plasma-generating gas used in the plasma treatment contains at least one of oxygen or nitrogen. Patent Literature 1 also discloses a plasma treatment detection indicator comprising a color-changing layer that comprises the ink composition formed on a base material.

Patent Literature 2 discloses an ink composition for detecting inert gas plasma treatment, comprising (1) at least one of anthraquinone colorants, azo colorants, and methine colorants; and (2) at least one of binder resins, cationic surfactants and extenders, the inert gas containing at least one selected from the group consisting of helium, neon, argon, krypton, and xenon. Patent Literature 2 also discloses a plasma treatment detection indicator in which a color-changing layer comprising the ink composition is formed on a base material.

However, the check method, using emission analysis or a traditional plasma treatment detection indicator may be insufficient in performance as an indicator for use in an electronic device production equipment. Specifically, because of the limitation to the measurement and analysis performed through the window provided to the electronic device production equipment, it tends to be difficult to perform efficient measurement or analysis with the check method using emission analysis when the inside of the electronic device production equipment cannot be thoroughly seen. Although the use of a traditional plasma treatment detection indicator is a convenient and excellent means for confirming the completion of plasma treatment through the color change of the color-changing layer, the organic colorants as a color-changing material may possibly lead to decreased cleanliness of the electronic device production equipment or contamination of electronic devices due to gasification of the organic colorants or scattering of the fine debris of the organic colorants caused by plasma treatment. The gasification of color-changing changing material may adversely affect the vacuum performance of the electronic device production equipment. In addition, because of the insufficient heat resistance of the traditional color-changing layer comprising organic colorants as a color-changing material, it is difficult to use it as an indicator when the electronic device production equipment has a high temperature.

Therefore, there has been a demand for the development of a plasma treatment detection indicator comprising a color-changing layer that changes color by plasma treatment, exhibiting excellent heat resistance with the gasification of the color-changing material or the scattering of the fine debris of the color-changing material caused by plasma treatment being suppressed to the extent that electronic device properties are not affected.

CITATION LIST

Patent Literature

Patent Literature 1: JP2013-98196A
Patent Literature 2: JP2013-95764A

SUMMARY OF INVENTION

Technical Problem

An object of the present invention is to provide an ink composition for detecting plasma treatment and for forming a color-changing layer that changes color by plasma treatment, the ink composition exhibiting excellent heat resistance, with the gasification of the color-changing layer or the scattering of the fine debris of the color-changing layer caused by plasma treatment being suppressed to the extent that electronic device properties are not affected. Another object of the present invention is to provide a plasma treatment detection indicator using the ink composition for detecting plasma treatment.

Solution to Problem

The present inventors conducted extensive research to achieve the object, and found that the use of specific metal oxide particles as a color-changing material contained in an ink composition for detecting plasma treatment achieves the object. The inventors have thus completed the present invention.

Specifically, the present invention relates to the following ink composition for detecting plasma treatment and plasma treatment detection indicator using the composition.

Item 1. An ink composition for detecting plasma treatment and for forming a color-changing layer that changes color by plasma treatment,
the ink composition comprising metal oxide particles containing at least one element selected from the group consisting of Mo, W, Sn, V, Ce, Te, and Bi, and
a binder resin.

Item 2. The ink composition for detecting plasma treatment according to Item 1, wherein the metal oxide particles contain at least one member selected from the group consisting of molybdenum(IV) oxide particles, molybdenum(VI) oxide particles, tungsten(VI) oxide particles, tin(IV) oxide particles, vanadium(II) oxide particles, vanadium(III) oxide particles, vanadium(IV) oxide particles, vanadium(V) oxide particles, cerium(IV) oxide particles, tellurium (IV) oxide particles, bismuth(III) oxide particles, bismuth(III) carbonate oxide particles, and vanadium(IV) oxide sulfate particles.

Item 3. The ink composition for detecting plasma treatment according to Item 1 or 2, wherein the metal oxide particles contain at least one member selected from the group consisting of molybdenum(VI) oxide particles, tungsten (VI) oxide particles, vanadium (III) oxide particles, vanadium (V) oxide particles, and bismuth(III) oxide particles.

Item 4. The ink composition for detecting plasma treatment according to any one of Items 1 to 3, wherein the metal oxide particles have a mean particle size of 50 µm or less.

Item 5. The ink composition for detecting plasma treatment according to any one of Items 1 to 4, wherein the binder resin contains at least one member selected from the group consisting of petroleum hydrocarbon resins, vinyl resins, butyral resins, alkyd resins, acrylic resins, epoxy resins, urethane resins, acrylonitrile resins, fluororesins, silicon resins, formalin resins, polyester resins, polyethylene resins, ketone resins, polyamide resins, maleic resins, coumarone resins, polyimide resins, polyetheretherketone resins, and alicyclic resins.

Item 6. The ink composition for detecting plasma treatment according to any one of Items 1 to 5, wherein the binder resin has a softening point of 70° C. or higher.

Item 7. A plasma treatment detection indicator comprising, on a base material, a color-changing layer formed of a cured coating film of the ink composition for detecting plasma treatment of any one of Items 1 to 6.

Item 8. The plasma treatment detection indicator according to Item 7, for use in an electronic device production equipment.

Item 9. The plasma treatment detection indicator according to Item 8, which has a shape that is identical to the shape of an electronic device substrate for use in the electronic device production equipment.

Item 10. The plasma treatment detection indicator according to Item 8 or 9, wherein the electronic device production equipment performs at least one plasma treatment selected from the group consisting of a film-forming step, an etching step, an ashing step, an impurity-adding step, and a washing step.

Item 11. The plasma treatment detection indicator according to any one of Items 7 to 10, comprising a non-color-changing layer that does not change color by plasma treatment.

Item 12. The plasma treatment detection indicator according to Item 11, wherein the non-color-changing layer contains at least one member selected from the group consisting of titanium (IV) oxide, zirconium(IV) oxide, yttrium(III) oxide, barium sulfate, magnesium oxide, silicon dioxide, alumina, aluminum, silver, yttrium, zirconium, titanium, and platinum.

Item 13. The plasma treatment detection indicator according to Item 11 or 12, wherein the non-color-changing layer and the color-changing layer are formed on the base material in sequence,
the non-color-changing layer is formed adjacent to the principal surface of the base material, and
the color-changing layer is formed adjacent to the principal surface of the non-color-changing layer.

Advantageous Effects of Invention

In a plasma treatment detection indicator obtained by using the ink composition for detecting plasma treatment of the present invention, specific metal oxide particles are used as a color-changing material contained in the color-changing layer. The color of the color-changing layer is chemically changed because the valence of the metal oxide particles is changed by plasma treatment. This suppresses the gasification of the color-changing layer or scattering of the fine debris of the color-changing layer caused by plasma treatment to the extent that electronic device properties are not affected. In addition, because the color-changing material comprises one or more inorganic components, the indicator exhibits heat resistance capable of resisting the process temperature applied in electronic device production. The indicator of the present invention is particularly useful as a plasma treatment detection indicator for use in an electronic device production equipment, which must be treated in a vacuum and high-temperature condition, as well as in a highly clean environment. Examples of electronic devices include semiconductors, light-emitting diodes (LED), laser diodes, power devices, solar batteries, liquid crystal displays, and organic EL displays.

BRIEF DESCRIPTION OF DRAWINGS

(a) shows the state of Example 1; and
(b) shows the state of prior art 1.

DESCRIPTION OF EMBODIMENTS

The following describes in detail the ink composition for detecting plasma treatment, and the plasma treatment detection indicator of the present invention.

Ink Composition for Detecting Plasma Treatment

The ink composition for detecting plasma treatment of the present invention (hereinafter sometimes referred to as "the ink composition of the present, invention") is used for forming a color-changing layer that changes color by plasma treatment, and is characterized by comprising metal oxide particles containing at least one element selected from the group consisting of Mo, W, Sn, V, Ce, Te, and Bi, and a binder resin.

In the plasma treatment detection indicator of the present invention (hereinafter sometimes referred to as "the indicator of the present invention") obtained by using the ink composition of the present invention, the color-changing layer, which is a cured coating film of the ink composition, contains specific metal oxide particles as a color-changing material. The color of the color-changing layer is chemically changed because the valence of the metal oxide particles is changed by plasma treatment. This suppresses the gasification of the color-changing layer or scattering of the fine debris of the color-changing layer caused by plasma treatment to the extent that electronic device properties are not affected. In addition, because the color-changing material comprises one or more inorganic components, the indicator exhibits heat resistance capable of resisting the process temperature applied in electronic device production.

The ink composition of the present invention comprises metal oxide particles containing at least, one element selected from the group consisting of Mo, W, Sn, V, Ce, Te, and Bi, and a binder resin. The ink composition further comprises a solvent, for dissolving the binder resin, and may additionally comprise known additives, such as a thickener, as optional components, to an extent that, the effect of the present invention is not affected. The following describes each component, constituting the ink composition of the present, invention.

Metal Oxide Particles

The metal oxide particles are at least one member selected from the group consisting of molybdenum(IV)) oxide particles, molybdenum(VI) oxide particles, tungsten(VI) oxide particles, tin (IV) oxide particles, vanadium (II) oxide particles, vanadium (III) oxide particles, vanadium(IV) oxide particles, vanadium(V) oxide particles, cerium(IV) oxide particles, tellurium (IV) oxide particles, bismuth(III) oxide particles, bismuth(III) carbonate oxide particles, and vanadium(IV) oxide sulfate particles. It is possible that the metal oxide particles contain a slight amount of crystalline water in the molecules, but it is preferable that the metal oxide particles contain no crystalline water to thus exclude the possibility of releasing water molecules (moisture gas).

In particular, in the present invention, a color change chemically occurs when the valence of the metal oxide particles is changed by plasma treatment. Unlike organic colorants, which have been previously used as color-changing materials, the gasification of the metal oxide particles or scattering of the fine debris of the metal oxide particles caused by plasma treatment is suppressed to the extent that electronic device properties are not affected. In addition, the metal oxide particles exhibit heat resistance capable of resisting the process temperature applied in electronic device production.

Of the above, in consideration of the color change by plasma treatment, the metal oxide particles are preferably at least one member selected from the group consisting of molybdenum(VI) oxide particles, tungsten(VI) oxide particles, vanadium(III) oxide particles, vanadium(V) oxide particles, and bismuth(III) oxide particles.

The mean particle size of the metal oxide particles is not limited. To improve the color change (sensitivity) by plasma treatment, the mean particle size is preferably 50 μm or less, and more preferably about 0.01 to 10 μm. The mean particle size as used herein is a value measured by a method using a laser diffraction/scattering particle size distribution measurement device (product name: Microtrac MT3000, produced by Nikkiso Co. Ltd.).

The amount of the metal oxide particles contained in the ink composition of the present invention is not limited, and is preferably 10 to 90 wt %, and more preferably 30 to 60 wt %. If the amount of the metal oxide particles is less than 10 wt %, the color change caused by plasma treatment may possibly be insufficient. If the amount of the metal oxide particles exceeds 90 wt %, the cost increases, and the adhesion strength of a color-changing layer to a base material, which is a dry coating film of the ink composition, may possibly decrease when the color-changing layer is formed on the base material.

Binder Resin

There is no limitation to the binder resin as long as the color-changing layer formed on a base material has excellent, adhesion strength on the base material. The binder resin may be, for example, at least one .member selected from the group consisting of petroleum hydrocarbon resins, vinyl resins, butyral resins, alkyd resins, acrylic resins, epoxy resins, urethane resins, acrylonitrile resins, fluororesins, silicon resins, formalin, resins, polyester resins, polyethylene resins, ketone resins, polyamide resins, maleic resins, coumarone resins, polyimide resins, polyetheretherketone resins, and alicyclic resins. These binder resins may be incorporated into the ink composition by being dissolved in a solvent mentioned later.

Of these binder resins, resins having a softening point of 70° C. or higher are preferable, and resins having a softening point of 130° C. or higher, such as polyimide resins, rosin-modified ketone resins, silicon resins, butyral resins, polyamide resins, and fluororesins, are more preferable. Of butyral resins, polyvinyl butyral resins (PVB resins) are preferable considering that they, in particular, cause less effect on the color change of the color-changing layer, have excellent heat resistance, and can suppress the gasification caused, by plasma treatment.

In addition to those listed above as examples of the binder resin, in the present, invention, it is also possible to use thermosetting resins, photo-curable resins, and the like. These resins, when used, are cured by polymerization or the like with the application of heat, light, or the like. Thus, the ink composition may contain a resin precursor that becomes a target binder resin when cured by polymerization or the like. Heat, light, or the like may be applied to the coating film of the ink composition, as mentioned below.

The amount of the binder resin contained in the ink composition of the present invention is not limited and may be adjusted depending on the type and the like of the binder resin. The amount is preferably 0.5 to 30 wt %, and more preferably 5 to 10 wt %. If the amount of the binder resin is less than 3 wt % or exceeds 15 wt.%, the adhesion strength of the color-changing layer to the base material may possibly decrease.

Solvent

The solvent is not limited as long as it dissolves the binder resin and imparts excellent applicability to the ink composition. For example, a petroleum-based solvent, is preferably used. In particular, ethylene glycol monobutyl ether (butyl cellosolve), ethylene glycol monoethyl ether (ethyl cellosolve), and the like are preferable.

The amount of the solvent contained in the ink composition of the present invention is not limited and may be adjusted depending on the type and the like of the binder resin. The amount is preferably 10 to 70 wt % and more preferably 25 to 40 wt %. If the amount of solvent is less than 10 wt % or exceeds 70 wt %, the applicability of the ink composition may decrease. If the solvent is contained in an excess amount, drying the ink composition, may possibly fake a long time.

Additives, Such as a Thickener

In addition to the above components, the ink composition of the present invention may further comprise known additives, such as a thickener, as optional components. It is preferable to use a thickener that thickens the ink composition to inhibit the sedimentation of the metal oxide particles, as well as to improve applicability.

For example, the thickener is preferably at least one member selected from silicate minerals and silicate compounds. Of these, silica is particularly preferable.

The amount of the thickener contained in the ink composition of the present invent .ion is not limited. When contained, the .amount is preferably 10 wt. % or less, and more preferably 3 to 6 wt %. When the amount of the thickener exceeds 10 wt %, the viscosity of the ink composition increases, possibly decreasing the applicability. When silica is contained as a thickener, a base-layer concealing property can be imparted to the color-changing layer. Based on the base-layer concealing property, it is possible to achieve an effect in which the color change of the color-changing layer is improved.

The ink composition of the present invention may be prepared by mixing and stirring the above components: using known methods.

Indicator for Detecting Plasma Treatment

The indicator of the present invention is characterized by comprising, on a base material, a color-changing layer formed of a cured coating film of the ink composition of the present invention. The cured coating film includes both an embodiment of a dry coating film formed by solvent removal and an embodiment of a cured coating film formed by curing a resin precursor by polymerization or the like with the application of heat, light, or the like.

The method for forming a color-changing layer is not limited as long as the method comprises forming a cured coating film of the ink composition on a base material. For example, a color-changing layer may be formed by applying the ink composition to a substrate, and evaporating the solvent, followed by drying in the atmosphere. Depending on the type of binder resin (and resin precursor), the application of heat, light, or the like may be performed instead of drying or in addition to drying.

Base Material

The base material is not particularly limited as long as the color-changing layer is formed thereon and as long as the base material can support the color-changing layer. Examples of usable base materials include metals or alloys, ceramic, quartz, glass, concrete, resins, fabrics (non-woven fabrics, woven fabrics, glass fiber filters, and other fiber sheets), and composite materials thereof. Those typically known as art electronic device substrate, such as silicon, gallium arsenide, silicon carbide, sapphire, glass, gallium nitride, and germanium, may also be used as the base material of the indicator of the present invention. The thickness of the base material can suitably be determined in accordance with the type of indicator.

As the above resins, any of thermoplastic resins and thermosetting resins may be used. Examples include PE (polyethylene) resins, PP (polypropylene) resins, PS (polystyrene) resins, AS (acrylonitrile-styrene) resins, ABS (acrylonitrile-butadiene-styrene copolymer) resins, vinyl resins, PMMA (acrylic-methacryl) resins, PET (polyethylene terephthalate) resins, PA (nylon) resins, POM (polyacetal) resins, PC (polycarbonate) resins, PBT (polybutylene terephthalate) resins, PPS (polyphenylenesulfide) resins, PI (polyimide) resins, PEI (polyetherimide) resins, PSF (polysulfone) resins, PTFE (Teflon (registered trademark)) resins, PCTFE (fluorine) resins, PAI (polyamidoimide) resins, PF (phenolic) resins, UF (urea) resins, MF (melamine) resins, DP (unsaturated polyester) resins, PU (polyurethane) resins, PDAP (allyl) resins, EP (epoxy) resin, SI (silicone) resins, FF (furan) resins, PEEK (polyetheretherketone) resins, and the like. Of these resins, PI resins, which have high heat resistance and which allow the color-changing layer to achieve excellent adhesion strength, are preferable.

Color-Changing Layer

The method for applying the ink composition to form a color-changing layer on a base material is not limited. It is possible to use, for example, a wide range of known coating methods, such as spin coating, slit coating, spray coating, and dip coating, and a wide range of known printing methods, such as silk-screen printing, gravure printing, offset printing, relief printing, and flexographic printing. In the present, invention, coating and application include the concepts of printing, dipping, and the like, in addition to coating and application.

After the ink composition is applied, the coating film is dried. The drying temperature is not limited, and is usually preferably about 80 to 200° C., and more preferably about 100 to 150° C.

The thickness of the color-changing layer of the indicator of the present invention is not limited. The thickness is preferably about 500 nut to 2 mm, and more preferably about 1 to 100 μm.

Non-Color-Changing Layer

To enhance the visibility of the color-changing layer, the indicator of the present invention may be provided with, as an underlayer, a non-color-changing layer that does not change color by plasma treatment. It is required that the non-color-changing layer be heat resistant, and the gasification of the non-color-changing layer be suppressed. The non-color-changing layer is preferably a white layer, a metal layer, and the like.

The white layer may be formed using, for example, titanium(IV) oxide, zirconium(IV) oxide, yttrium(III) oxide, barium sulfate, magnesium oxide, silicon dioxide, or alumina.

The metal layer may be formed using, for example, aluminum, silver, yttrium, zirconium, titanium, or platinum.

Examples of the method for forming a non-color-changing layer include physical vapor deposition (PVD), chemical vapor deposition (CVD), and sputtering. The layer may also be formed by preparing a slurry containing a substance that forms a non-color-changing layer, applying the slurry onto a substrate, evaporating the solvent, and calcining the substrate in the atmosphere. Examples of slurry application and printing methods include a wide range of known coating methods and printing methods, such as spin coating, slit coating, spray coating, dip coating, silk-screen printing, gravure printing, offset printing, relief printing, and flexographic printing. The thickness of the non-color-changing layer can suitably be determined in accordance with the type of indicator.

In the present invention, any combination of the color-changing layer and the non-color-changing layer is possible, as long as the completion of the plasma treatment is confirmed. For example, the color-changing layer and the non-color-changing layer may be formed such that the color difference between the color-changing layer and the non-color-changing layer is identified after the color-changing layer undergoes a color change, or such that the color difference between the color-changing layer and the non-color-changing layer is eliminated after color change. In the present invention, it is preferable to form a color-changing layer and a non-color-changing layer particularly such that the color difference between the color-changing layer and the non-color-changing layer is identified after the color-changing layer undergoes a color change.

To enable the identification of color difference, a color-changing layer and a non-color-changing layer may be formed, for example, such that at least one of characters, patterns, and symbols appears because of the change in color of the color-changing layer. In the present invention, characters, patterns, and symbols include any information that signals a change in color. These characters, etc., may be suitably designed in accordance with the intended use or other purposes.

The color-changing layer and the non-color-changing layer before color change may have different colors. Both of the color-changing layer and the non-color-changing layer may have, for example, substantially the same color, and color difference (contrast) between the layers may be identified for the first time after color change.

In the present invention, examples of preferable embodiments of the layered structure include (i) an indicator in which the color-changing layer is formed adjacent to at least one principal surface of a base material; and (ii) an indicator in which the non-color-changing layer and the color-changing layer are formed in sequence on a base material, with the non-color-changing layer formed adjacent to the principal surface of the base material and the color-changing layer formed adjacent to the principal surface of the non-color-changing layer.

Adhesion Layer

The indicator of the present invention may optionally comprise an adhesion layer on a back surface of the base material (a surface opposite to the surface on which the color-changing layer is formed). It is preferable that an adhesion layer be formed on the back surface of the base material, because the indicator of the present invention is thereby securely fixed to a desired portion in the plasma treatment device (such as an object to be subjected to plasma treatment, the bottom of the device).

The components of the adhesion layer are preferably those whose gasification by plasma treatment is suppressed. As such components, for example, special adhesives are preferable, and of these, silicone-based adhesives are preferable.

Shape of the Indicator of the Present Invention

The shape of the indicator of the present invention is not particularly limited, and a vide range of shapes adopted for known plasma treatment, detection indicators can be used. When the indicator of the present invention has a shape that is identical to the shape of an electronic device substrate for use in an electronic device production equipment, it becomes possible to easily detect whether plasma treatment is homogeneously performed on the entire electronic device substrate using the indicator as a "dummy substrate."

As used herein, the phrase "the indicator of the present invention has a shape that is identical to the shape of an electronic device substrate for use in an electronic device production equipment" includes both of the following meanings: (i) the shape of the indicator is completely the same as the shape of the electronic device substrate used in an electronic device production equipment; and (ii) the shape of the indicator is substantially the same as the shape of the electronic device substrate used in an electronic device production equipment to the degree that the indicator can be placed (set) in the setting position on the electronic device substrate in the electronic device production equipment that perform plasma treatment.

The phrase "substantially the same" in meaning (ii) above includes, for example, the following meaning: the difference in length between the principal surface of the electronic device substrate (when the shape of the principal surface of the substrate is circular, then the diameter; when the shape of the principal surface of the substrate is square, rectangular, or the like, then the length and width) and the principal surface of the indicator of the present invention is within ±5.0 mm; and the difference in thickness between the electronic device substrate and the indicator of the present invention is within about ±1000 μm.

The indicator of the present invention is not limited to the use in an electronic device production equipment. However, when used in an electronic device production equipment, the indicator is preferably used in an electronic device production equipment that performs at least one step selected from the group consisting of a film-forming step, an etching step, an ashing step, an impurity-adding step, and a washing step by plasma treatment.

Plasma

The plasma is not particularly limited, and plasma generated with a plasma-generating gas may be used. Of plasma, preferable is plasma that, is generated with at least, one plasma-generating gas selected from the group consisting of oxygen, nitrogen, hydrogen, chlorine, argon, silane, ammonia, sulfur bromide, boron trichloride, hydrogen bromide, water vapor, nitrous oxide, tetraethoxysilane, nitrogen trifluoride, carbon tetrafluoride, perfluoro cyclobutane, difluoromethane, trifluoromethane, carbon tetrachloride, silicon tetrachloride, sulfur hexafluoride, hexafluoroethane, titanium tetrachloride, dichlorosilane, trimethylgallium, trimethylindium, and trimethylaluminum. Of these plasma-generating gasses, particularly preferable is at least one member selected from the group consisting of carbon tetrafluoride, perfluoro cyclobutane, trifluoromethane, sulfur hexafluoride, and a mixed gas of argon and oxygen.

Plasma can be generated with a plasma treatment apparatus (an apparatus for performing plasma treatment by applying alternating-current power, direct-current power, pulse power, high-frequency power, microwave power, or the like in an atmosphere containing a plasma-generating gas to generate plasma). Particularly in an electronic device production equipment, plasma treatment is used in a film-forming step, an etching step, an ashing step, an impurity-adding step, a washing step, and the like described later.

In a film-forming step, for example, a film can be grown on a semiconductor wafer at a low temperature of 400° C. or lower at a relatively high growth rate by using both plasma and thermal energy in plasma CVD (chemical vapor deposition). Specifically, a material gas is introduced into a depressurized reaction chamber, and the gas is radical ionized by plasma excitation to allow a reaction. Plasma CVD include capacitively coupled plasma-type (anodic bonding-type or parallel plate-type), inductively coupled plasma-type, and ECR (electron cyclotron resonance) plasma-type.

Another film-forming step is a step by sputtering. A specific example is that when tens to thousands of voltage is applied between a semiconductor wafer and a target in an inert gas (e.g., Ar) of about 1 Torr to $10^{-4}$ Torr in a high-frequency discharge sputtering apparatus, ionized Ar is accelerated toward the target and collides with the target; this causes the target substance to be sputtered and deposited on the semiconductor wafer. At this stage, high-energy $\gamma^-$ electrons are generated from the target at the same time. When colliding with Ar atoms, the $\gamma^-$ electrons ionize Ar atoms ($Ar^+$), thereby maintaining plasma.

Another film-forming step is a step by ion plating. A specific example is that the inside is made a high-vacuum condition of about $10^{-5}$ Torr to $10^{-7}$ Torr, and then an inert gas (e.g., Ar) or a reactive gas (e.g., nitrogen and hydrocarbon) is injected thereinto. Then, from the thermionic cathode (electron gun) of a processing apparatus, an electron beam is discharged toward the deposition material to generate plasma in which ions and electrons are separately present. Subsequently, a metal is heated and vaporized at a high temperature by an electron beam, and the vaporized metal particles are subjected to a positive voltage, allowing the electrons and the metal particles to collide in plasma. This causes the metal particles to become positive ions, which proceed toward the object to be processed; at the same time, the metal particles bind to a reactive gas to promote a chemical reaction. The particles, for which a chemical reaction has been promoted, are accelerated toward the object to be processed to which negative electrons have been added, collide with the object with high energy, and are thereby deposited as a metal compound on the surface. A vapor deposition method similar to ion plating is also an example of a film-forming step.

In addition, the oxidizing and nitriding step includes a method for converting the semiconductor wafer surface into an oxide film by plasma oxidation using, for example, ECR plasma or surface wave plasma; and a method for converting the semiconductor wafer surface into a nitride film by introducing an ammonia gas, and dissociating, decomposing, and ionizing the ammonia gas by plasma excitation.

In the etching step, for example, in a reactivity ion etching apparatus (RIE), circular plate electrodes are placed in parallel, and a reaction gas is introduced into a depressurized reaction chamber (chamber). The introduced reaction gas is then radicalized or ionized by plasma excitation such that the radicals or ions are present between the electrodes. The etching step uses the effects of both etching that, causes a substance on the semiconductor wafer to volatize by using a chemical reaction between these radicals or ions and the material; and physical sputtering. As a plasma etching apparatus, a barrel-type (cylindrical) etching apparatus, as well as the parallel plate-type etching apparatus, can be used.

Another etching step is reverse sputtering. Reverse sputtering is similar in principle to sputtering. Reverse sputtering is an etching method in which ionized Ar in plasma is allowed to collide with the semiconductor wafer. Ion beam etching, similar to reverse sputtering, is also an example of the etching step.

In the ashing step, for example, a photoresist is decomposed and volatilized using oxygen plasma obtained by the plasma excitation of oxygen gas under reduced pressure.

In the impurity-adding step, for example, a gas containing impurity atoms for doping is introduced into a depressurized chamber, and plasma is excited to ionize the impurities. A negative bias voltage is applied to the semiconductor wafer to dope the wafer with the impurity ions.

The washing step is a step for removing foreign materials adhered to the semiconductor wafer without, causing damage to the wafer before performing each step on the wafer. Examples include plasma washing that, causes a chemical reaction with oxygen gas plasma, and plasma washing (reverse sputtering) that physically removes foreign materials by inert gas (e.g., argon) plasma.

EXAMPLES

The following describes the present invention in detail by showing Examples and Comparative Examples. However, the present invention is not limited to the Examples.

Examples 1 to 5 and Comparative Example 1

Ink compositions having the formulation shown in Table 1 below were prepared and applied to a polyimide film and dried, thereby forming a 20-μm color-changing layer on the polyimide film.

TABLE 1

| Formulation | Example 1 PVB | Example 2 Nitrocellulose | Example 3 Styrene acryl | Example 4 Polyamide | Example 5 Phenol | Comp. Ex. 1 No binder |
|---|---|---|---|---|---|---|
| Bismuth oxide | 30.00 | 30.00 | 30.00 | 30.00 | 30.00 | 30.00 |
| Silica | 3.00 | 3.00 | 3.00 | 3.00 | 3.00 | 3.00 |
| PVB | 7.00 | | | | | |
| Nitrocellulose | | 7.00 | | | | |
| Styrene acrylic resin | | | 7.00 | | | |
| Polyamide resin | | | | 7.00 | | |
| Phenolic resin | | | | | 7.00 | |
| Butyl cellosolve | 60.00 | 60.00 | 60.00 | 60.00 | 60.00 | 67.00 |
| Total | 100.00 | 100.00 | 100.00 | 100.00 | 100.00 | 100.00 |
| Color change in color-changing layer | ○ | ○ | ○ | ○ | X | X (Unmeasurable) |
| Delamination of color-changing layer | ○ | X | ○ | ○ | ○ | X |

Specifically, each ink composition for detecting plasma treatment was printed on a polyimide film, which is a base material, by silk-screen printing, and each coating film was dried at 170° C. for 10 minutes to produce an indicator.

Test Example 1

Figure 1:
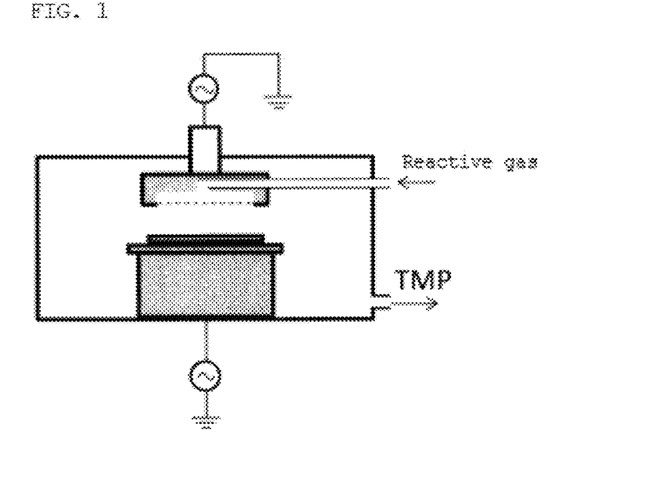
FIG. 1 is a schematic cross-sectional view of the capacitively coupled plasma-type (parallel plate-type) plasma etching apparatus (using a high-frequency power source (13.56 MHz)) used in Test Example 1. The "TMP" in the figure is an abbreviation for turbo-molecular pump.

FIG. 1 is a schematic cross-sectional view of a CCP-type (CCP: capacitively coupled plasma) plasma etching apparatus.

The apparatus is provided with parallel-plate electrodes inside a vacuum vessel, and the upper electrode has a shower structure, by which a reactive gas is supplied to the surface of the object to be treated in a shower-like manner.

When etching is actually performed, the vacuum vessel is degassed, and then a reactive gas is introduced from the shower part of the upper electrode. High-frequency power supplied from the upper electrode generates plasma in the space of the parallel-plate electrodes, and the generated excited species cause a chemical reaction, which etches the surface of the object to be treated.

In Test Example 1, the indicators produced in Examples 1 to 5 and Comparative Example 1 were placed in this apparatus, carbon tetrafluoride gas ($CF_4$) as a reactive gas was introduced thereinto, and plasma treatment was performed. The color change of the color-changing layer of each indicator (measurement of color difference ΔE before and after the treatment) and delamination were evaluated.

Table 2 shows the plasma treatment conditions.

TABLE 2

| Gas flow rate (sccm) | Pressure (Pa) | High frequency power (W) | Treatment time (min) |
|---|---|---|---|
| 10 | 10 | 50 | 10 |

Table 1 shows the results of color change. The following are evaluation criteria for color change:
O: Color difference ΔE>15
X: Color difference ΔE<15
Table 1 shows the results of delamination. The following are evaluation criteria for delamination:
O: Delamination of the color-changing layer did not occur even when the color-changing layer was touched after plasma treatment.
X: Delamination of the color-changing layer occurred when the color-changing layer was touched after plasma treatment.

Test Example 2

The indicator produced in Example 1 and a plasma treatment detection indicator containing an organic colorant in its color-changing layer according to prior art. 1 (Wahl Instruments. Inc., Temp-plate, 101-6-215C) were prepared, and their outgassing characteristics when the temperature was increased were compared.

Figure 2:
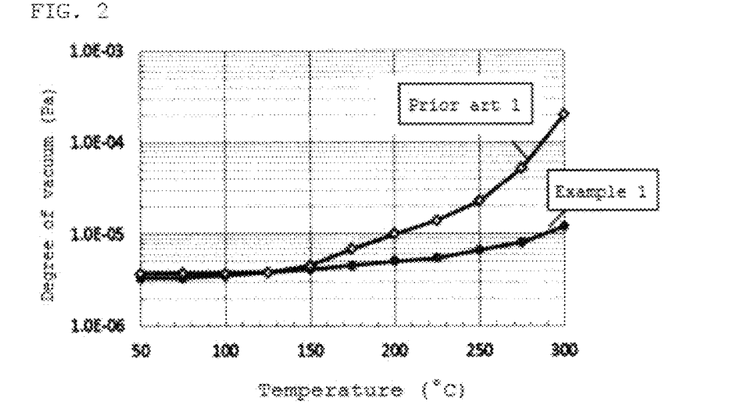
FIG. 2 is a graph showing the relationship between temperature increase and the degree of vacuum in Test Example 2.

Specifically, the indicator of Example 1 and the indicator of prior art 1 were individually mounted on a stage: whose temperature could be increased, and individually placed in a vacuum apparatus. After the inside of the apparatus was evacuated to achieve a degree of vacuum of 1.0 E -6 Pa, the outgassing characteristics were studied based on the change in the degree of vacuum inside the vacuum apparatus while the temperature of the stage was raised at 30° C./min. FIG. 2 shows the results of the outgassing characteristics.

As is clear from the results shown in FIG. 2, although the indicator of prior art 1 exhibited a great change in the degree of vacuum over the temperature of 150 to 200° C., the indicator of Example 1 exhibited less change in the degree of vacuum than the indicator of prior art 1. This reveals that the indicator containing metal oxide particles as a color-changing material according to the present, invention releases less gas at the time of temperature increase than the indicator containing an organic colorlant in its color-changing layer according to prior art 1.

Figure 3:
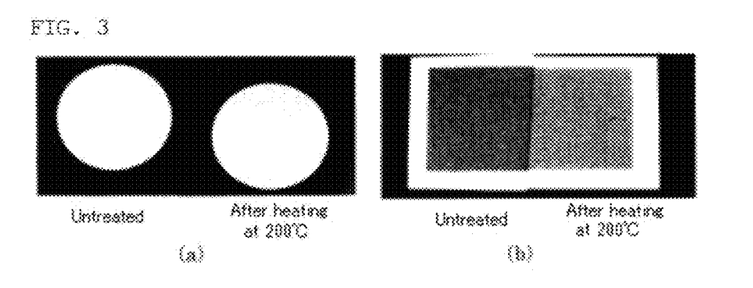
FIG. 3 shows the state of the color-changing layer when the temperature increased to 200° C. in Test Example 2.

As is also clear from FIG. 3, which shows the results of an observation of the color of each sample after temperature increase, although the indicator according to prior art 1 ((b) in FIG. 3) underwent a color change due to heat, the indicator of Example 1 ((a) of FIG. 3) did not undergo a color change due to heat.

This is presumably due to the following reasons. In the indicator according to prior art 1, which contains an organic colorant in its color-changing layer, the organic substance underwent decomposition at around 200° C., generating outgassing and causing the organic: colorant to undergo a color change; in contrast, the indicator produced in Example 1, which contains metal oxide particles (inorganic substance) in its color-changing layer, had excellent outgassing characteristics and heat resistance.

The invention claimed is:

1. An ink composition for detecting plasma treatment and for forming a color-changing layer that changes color by plasma treatment,
the ink composition comprising:
metal oxide particles containing at least one element selected from the group consisting of Mo, W, V, Ce, Te, and Bi, and
a binder resin,
wherein the only elements contained in the metal oxide particles are Mo, W, V, Ce, Te, and Bi,
wherein the amount of the metal oxide particles contained in the ink composition is 30 to 60 wt %, and
wherein the valence of the metal oxide fine particles is configured to be changed by the plasma treatment.

2. The ink composition for detecting plasma treatment according to claim 1, wherein the metal oxide particles contain at least one member selected from the group consisting of molybdenum(IV) oxide particles, molybdenum(VI) oxide particles, tungsten(VI) oxide particles, vanadium (II) oxide particles, vanadium(III) oxide particles, vanadium (IV) oxide particles, vanadium(V) oxide particles, cerium (IV) oxide particles, tellurium (IV) oxide particles, bismuth (III) oxide particles, bismuth(III) carbonate oxide particles, and vanadium(IV) oxide sulfate particles.

3. The ink composition for detecting plasma treatment according to claim 1 wherein the metal oxide particles contain at least one member selected from the group consisting of molybdenum(VI) oxide particles, tungsten(VI) oxide particles, vanadium(III) oxide particles, vanadium(V) oxide particles, and bismuth(III) oxide particles.

4. The ink composition for detecting plasma treatment according to claim 2, wherein the metal oxide particles contain at least one member selected from the group consisting of molybdenum(VI) oxide particles, tungsten(VI) oxide particles, vanadium(III) oxide particles, vanadium(V) oxide particles, and bismuth(III) oxide particles.

5. The ink composition for detecting plasma treatment according to claim 1, wherein the metal oxide particles have a mean particle size of 50 μm or less.

6. The ink composition for detecting plasma treatment according to claim 1, wherein the binder resin contains at least one member selected from the group consisting of petroleum hydrocarbon resins, vinyl resins, butyral resins, alkyd resins, acrylic resins, epoxy resins, urethane resins, acrylonitrile resins, fluororesins, silicon resins, formalin resins, polyester resins, polyethylene resins, ketone resins, polyamide resins, maleic resins, coumarone resins, polyimide resins, polyetheretherketone resins, and alicyclic resins.

7. The ink composition for detecting plasma treatment according to claim 1, wherein the binder resin has a softening point of 70° C. or higher.

8. A plasma treatment detection indicator comprising, on a base material, a color-changing layer formed of a cured coating film of the ink composition for detecting plasma treatment of claim 1.

9. The plasma treatment detection indicator according to claim 8, for use in an electronic device production equipment.

10. The plasma treatment detection indicator according to claim 9, which has a shape that is identical to the shape of an electronic device substrate for use in the electronic device production equipment.

11. The plasma treatment detection indicator according to claim 9, wherein the electronic device production equipment performs at least one plasma treatment selected from the group consisting of a film-forming step, an etching step, an ashing step, an impurity-adding step, and a washing step.

12. The plasma treatment detection indicator according to claim 10, wherein the electronic device production equipment performs at least one plasma treatment selected from the group consisting of a film-forming step, an etching step, an ashing step, an impurity-adding step, and a washing step.

13. The plasma treatment detection indicator according to claim 8, comprising a non-color-changing layer that does not change color by plasma treatment.

14. The plasma treatment detection indicator according to claim 13, wherein the non-color-changing layer contains at least one member selected from the group consisting of titanium(IV) oxide, zirconium(IV) oxide, yttrium(III) oxide, barium sulfate, magnesium oxide, silicon dioxide, alumina, aluminum, silver, yttrium, zirconium, titanium, and platinum.

15. The plasma treatment detection indicator according to claim 13, wherein the non-color-changing layer and the color-changing layer are formed on the base material in sequence,
   the non-color-changing layer is formed adjacent to the principal surface of the base material, and
   the color-changing layer is formed adjacent to the principal surface of the non-color-changing layer.

16. The plasma treatment detection indicator according to claim 14, wherein the non-color-changing layer and the color-changing layer are formed on the base material in sequence,
   the non-color-changing layer is formed adjacent to the principal surface of the base material, and
   the color-changing layer is formed adjacent to the principal surface of the non-color-changing layer.

* * * * *